United States Patent
Zhang et al.

(10) Patent No.: US 7,092,756 B2
(45) Date of Patent: Aug. 15, 2006

(54) AUTOCAPTURE PACING/SENSING CONFIGURATION

(75) Inventors: Geng Zhang, Vadnais Heights, MN (US); Jungkuk Kim, Roseville, MN (US); Qingsheng Zhu, Little Canada, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/206,329

(22) Filed: Dec. 8, 1998

(65) Prior Publication Data

US 2002/0049477 A1    Apr. 25, 2002

(51) Int. Cl.
*A61N 1/362* (2006.01)
(52) U.S. Cl. ...................................................... 607/13
(58) Field of Classification Search ................. 607/13, 607/11, 28
See application file for complete search history.

(56) References Cited

U.S. PATENT DOCUMENTS

| | | | |
|---|---|---|---|
| 4,549,548 A * | 10/1985 | Wittkampf et al. ........... | 607/27 |
| 4,991,583 A * | 2/1991 | Silvian ......................... | 607/13 |
| 5,222,483 A | 6/1993 | Plisek | |
| 5,222,493 A | 6/1993 | Sholder | |
| 5,324,310 A * | 6/1994 | Greeninger et al. .......... | 607/28 |
| 5,690,683 A * | 11/1997 | Haefner et al. ............... | 607/13 |
| 5,800,465 A * | 9/1998 | Thompson et al. ............ | 607/9 |
| 5,843,136 A * | 12/1998 | Zhu et al. ..................... | 607/13 |
| 6,044,296 A * | 3/2000 | Zhu et al. ..................... | 607/13 |

* cited by examiner

*Primary Examiner*—George R. Evanisko
(74) *Attorney, Agent, or Firm*—Nikolai & Mersereau, P.A.; C. G. Mersereau

(57) ABSTRACT

A cardiac pacing system that enhances the ability of a cardiac pacer to automatically detect whether a pacing stimulus results in heart capture or contraction. The cardiac pacing system includes a pacing circuit that attenuates polarization voltages or "afterpotential" which develop at the heart tissue/electrode interface following the delivery of a stimulus to the heart tissue, which thereby allows the pacing electrodes to be utilized to sense an evoked response to the pacing stimulus. The cardiac pacing system utilizes the pacing electrodes to sense an evoked response, thereby eliminating the necessity for an indifferent electrode to sense an evoked response. The present invention allows accurate detection of an evoked response of the heart, to thereby determine whether each pacing stimulus results in capture.

32 Claims, 9 Drawing Sheets

AUTOCAPTURE PACING/SENSING CONFIGURATION

BACKGROUND OF THE INVENTION

I. Field of the Invention

The present invention relates generally to the field of cardiac rhythm management devices, including atrial, ventricular, and dual chamber pacemakers. More specifically, the present invention relates to a cardiac pacing system that improves the ability to automatically detect whether a pacing stimulus results in heart capture or contraction. The cardiac pacing system includes a pacing/sensing circuit that attenuates polarization voltages or "afterpotentials" which develop at the heart tissue/electrode interface following the delivery of a stimulus to the heart tissue. The pacing/sensing circuit of the present invention may utilize the pacing electrodes to sense a response evoked by the pacing stimulus. Thus, the present invention allows accurate detection of an evoked response of the heart, to thereby determine whether each pacing stimulus results in capture.

II. Discussion of the Prior Art

Cardiac pacers have enjoyed widespread use and popularity through time as a means for supplanting some or all of an abnormal heart's natural pacing functions. The various heart abnormalities remedied by pacemakers include total or partial heart block, arrhythmias, myocardial infarctions, congestive heart failure, congenital heart disorders, and various other rhythm disturbances within the heart. The general components of a cardiac pacemaker include an electronic pulse generator for generating stimulus pulses to the heart coupled to an electrode lead arrangement (unipolar or bipolar) positioned adjacent or within a preselected heart chamber for delivering pacing stimulus pulses.

Regardless of the type of cardiac pacemaker employed to restore the heart's natural rhythm (ie: ventricular pacing, atrial pacing, or dual chamber pacing in both the atrium and ventricle), each type operates to stimulate excitable heart tissue cells adjacent to the electrode of the pacing lead employed with the pacemaker, which may or may not result in capture. Myocardial response to stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is significantly greater than the concentration of sodium ions inside the cell membrane, while the concentration of potassium ions outside the cell membrane is significantly less than the concentration of potassium ions inside the cell membrane. The selective permeability of each myocardial cell also retains other negative particles within the cell membrane such that the inside of the cell membrane is negatively charged with respect to the outside when the cell is at rest. When a stimulus is applied to the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibril of the cell. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is re-polarized with a negative charge within the cell membrane. This causes the cell membrane to relax and return to the fully extended state, referred to as diastole.

In a normal heart, the sino-atrial (SA) node initiates the myocardial stimulation of the atrium. The SA node comprises a bundle of unique cells disposed within the roof of the right atrium. Each cell membrane of the SA node has a characteristic tendency to leak ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole wherein the atria contract to empty blood into the ventricles. The atrial depolarization from the SA node is detected by the atrio-ventricular (AV) node which, in turn, communicates the depolarization impulse into the ventricles via the Bundle of His and Purkinje fibers following a brief conduction delay. In this fashion, ventricular systole lags behind atrial systole such that the blood from the ventricles pumps through the body and lungs after being filled by the atria. Atrial and ventricular diastole follow wherein the myocardium is re-polarized and the heart muscle relaxed in preparation for the next cardiac cycle. It is when this system fails or functions abnormally that a cardiac pacer may be needed to deliver an electronic pacing stimulus for selectively depolarizing the myocardium of the heart so as to maintain proper heart rate and synchronization of the filling and contraction of the atrial and ventricular chambers of the heart.

The success of a pacing stimulus in depolarizing or "capturing" the selected chamber of the heart hinges on whether the current of the pacing stimulus as delivered to the myocardium exceeds a threshold value. This threshold value, referred to as the capture threshold, is related to the electrical field intensity required to alter the permeability of the myocardial cells to thereby initiate cell depolarization. If the local electrical field associated with the pacing stimulus does not exceed the capture threshold, then the permeability of the myocardial cells will not be altered enough and thus no depolarization will result. If, on the other hand, the local electrical field associated with the pacing stimulus exceeds the capture threshold, then the permeability of the myocardial cells will be altered sufficiently such that depolarization will result.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at level higher than necessary to effect capture.

The ability of a pacemaker to detect capture is desirable in that delivering stimulation pulses having energy far in excess of the patient's capture threshold is wasteful of the pacemaker's limited power supply. In order to minimize current drain on the power supply, it is desirable to automatically adjust the pacemaker such that the amount of stimulation energy delivered to the myocardium is maintained at the lowest level that will reliably capture the heart. To accomplish this, a process known as "capture verification" must be performed wherein the pacemaker monitors to determine whether an evoked depolarization occurs in the preselected heart chamber following the delivery of each pacing stimulus pulse to the preselected chamber of the heart.

The conventional pacemaker typically includes a pacing output circuit designed to selectively generate and deliver stimulus pulses through a lead to one or more electrodes positioned in the heart of a patient. The pacing output circuit includes a power supply, switches, a pacing charge storage capacitor, and a coupling capacitor, all of which cooperatively operate under the direction of a controller to perform a charging cycle, a pacing cycle, and a recharging cycle. The capacitance of the pacing charge storage capacitor typically ranges between 10–30 microfarads so as to develop a sufficient pacing charge for stimulating the heart. The capacitance of the coupling capacitor typically ranges between 15 to 40 microfarads with 33 microfarads being typical. A capacitor having a capacitance in this range was believed necessary to deliver sufficient energy to the heart.

The charging cycle involves manipulation of the switches such that the pacing charge storage capacitor is charged up to a predetermined voltage level. The pacing cycle involves manipulating the switches such that the voltage within the pacing charge storage capacitor may be discharged through the coupling capacitor to the electrodes of the pacemaker. The recharging cycle involves further manipulation of the switches for a predetermined period of time following the pacing pulse to allow the coupling capacitor to be discharged.

While the conventional pacing circuit is generally effective in delivering stimulus pulses to a selected chamber of the heart, it has been found that the detection of evoked depolarization or "capture verification" is rendered very difficult due to polarization voltages or "afterpotential" which develop at the heart tissue/electrode interface following the application of the stimulation pulses. The ability to verify capture is further affected by other variables including patient activity, body position, drugs being used, lead movement, noise etc.

In the past, the large capacitance of coupling capacitor was believed necessary in order to sufficiently block any DC components from the heart and to minimize pace pulse voltage droop. However, the large capacitance of the coupling capacitor causes a charge dissipation or "afterpotential" which is relatively large (100 mV or greater) and which decays exponentially over a relatively long period of time (100 milliseconds). This is particularly troublesome due to the fact that the evoked potential of the heart tissue is small in amplitude relative to the polarization voltage or "afterpotential" (100 mV). The amplitude of the evoked potential corresponding to a P-wave typically ranges between 1–5 mV and the amplitude of the evoked potential corresponding to an R-wave typically ranges between 5–20 mV.

Further, the long decay period of the polarization voltage or "afterpotential" effectively masks the evoked potential, which typically begins within approximately (10–40) milliseconds after the stimulation pulse to a selected chamber of the heart. It will be appreciated that this creates difficulty in detecting the evoked response of the heart following the delivery of stimulus pulses. In that evoked response is indicative of capture, the undesirable masking of the evoked response by "afterpotential" thus hampers the ability of the pacemaker to conduct automatic capture verification. Hence, there is a need for a cardiac pacing system that decreases and/or shortens the pacing afterpotential with minimal increase of the leading edge voltage pacing threshold. It is also desirable to reduce the number or complexity of the implanted components and, thus, there is a need for a pacing system having a pacing/sensing circuit that minimizes the number of required electrodes positioned within the heart for sensing a response evoked by a pacing stimulus directed to a preselected chamber of the heart.

Sholder in U.S. Pat. No. 5,222,483 recognizes that sensing a signal for verification of capture is extremely difficult because of the saturation voltage present following the generation of a stimulation pulse, which makes it difficult to accurately detect the voltage representing P-waves while discriminating against other signals present in the atrium. Sholder describes a capture verification circuit that requires an indifferent electrode disposed on the front or back of the connector top of the pacemaker or alternatively positioned on an additional lead or added to one of the pacing leads. The capture sensing lead and/or indifferent electrode required by Sholder increases the complexity and required components of the pacing system and may increase the cost thereof.

Hence, there is a need for a cardiac pacing system that attenuates polarization voltages or "afterpotentials" which develop at the heart tissue/electrode interface following the delivery of a stimulus to the heart tissue, and which minimizes the number of required components of the cardiac pacing system. The present invention meets these needs.

SUMMARY OF THE INVENTION

In accordance with a broad aspect of the present invention, the purpose of the present invention is to provide a cardiac pacing system that attenuates, decreases and shortens pacing afterpotentials without significantly increasing the leading edge voltage pacing threshold and which may operate with a plurality of unipolar or bipolar leads without the necessity of a separate capture sensing lead and/or indifferent electrode. Those skilled in the art will appreciate that the pacing/sensing circuit of the present invention may be utilized to determine whether a pacing stimulus directed to a selected atrium or ventricle evokes a response to the pacing stimulus. The preferred embodiment of the cardiac pacing system of the present invention includes an atrial pacing/sensing lead and a ventricular pacing/sensing lead electrically coupled to a cardiac pacer, means for pacing in the atrium and/or ventricle, means for sensing an evoked response in the atrium and/or ventricle electrically coupled to the atrial and ventricular leads, and afterpotential attenuation means for attenuating afterpotentials which results due to the application of a pacing stimulus to the heart by the cardiac pacer.

In the preferred embodiment the atrial lead may include an atrial tip electrode and an atrial ring electrode of known suitable construction, and the ventricular lead may include a ventricular tip electrode and a ventricular ring electrode of known suitable construction. The atrial lead's electrodes may be used for unipolar (pacing between one atrial electrode and the pacer's can) or bipolar pacing (pacing between two of the lead's electrodes). An evoked response in the atrium may be detected by sensing between the atrial ring electrode and ventricular tip electrode for an associated output. Alternatively, as further described below in greater detail, other pacing/sensing configurations may be implemented to determine whether a pacing stimulus to the atrium evokes a response in the atrium. Likewise, various pacing/sensing configurations described below in greater detail may be implemented to determine whether a pacing stimulus to the ventricle evokes a response in the ventricle.

The afterpotential attenuation means of the cardiac pacing system of the present invention is electrically coupled to the means for pacing and includes an improved coupling capacitor arrangement that differs from the conventional coupling capacitor of the conventional pacing/sensing circuit. The afterpotential attenuation means includes first coupling capacitor means for attenuating afterpotentials operatively coupled to second coupling capacitor means for blocking DC components, and also includes switching means for selectively coupling said second coupling capacitor means in series with said first coupling capacitor means so as to reduce the effective capacitance of said second capacitor means. Suitable afterpotential attenuating means are described in greater detail in co-pending applications Ser. Nos. 09/070,158, filed Apr. 30, 1998, Ser. No. 09/088,864, filed Jun. 2, 1998, and Ser. No. 08/977,272, filed Nov. 24, 1997, each of which have been assigned to the same assignee as the present application, the entire disclosures of which are incorporated herein by reference for any purpose.

OBJECTS

It is accordingly a principal object of the present invention to provide a cardiac pacing system for use with unipolar or bipolar atrial and ventricular pacing and sensing leads, which attenuates and shortens afterpotential and thereby enhances the detection of an evoked response in a preselected chamber of the heart.

Another object of the present invention is to provide a cardiac pacing system that may utilize the pacing electrodes of a bipolar atrial lead and bipolar ventricular lead to both pace and sense an evoked response in a preselected chamber of the heart.

Still another object of the present invention is to provide a cardiac pacing system that reduces the required blanking period and attenuates afterpotential developed at the pacing electrodes.

These and other objects and advantages of the present invention will be readily apparent to those skilled in the art from a review of the following detailed description of the preferred embodiment in conjunction with the accompanying claims and drawings in which like numerals in the several views refer to corresponding parts.

DESCRIPTION OF THE PREFERRED EMBODIMENT

Figure 1:
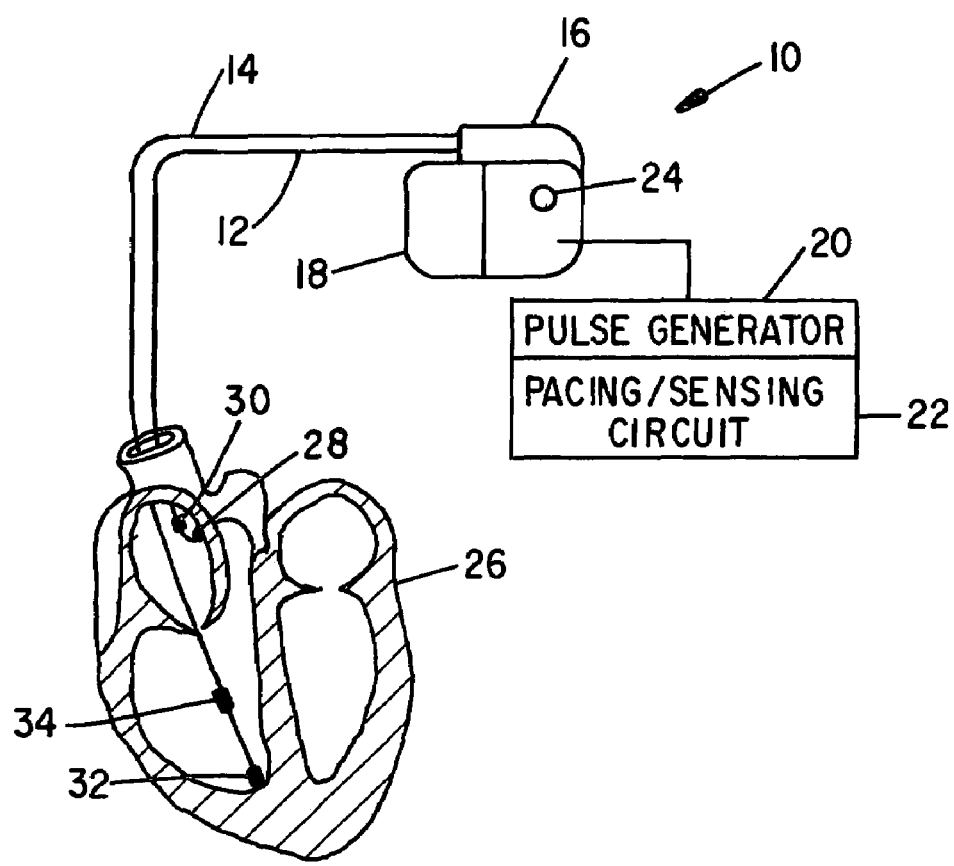
FIG. 1 is a block diagram depicting a cardiac pacing system in accordance with the present invention.

Referring first to FIG. 1, the cardiac pacing system of the present invention is shown generally and includes a cardiac pacer 10, atrial lead 12 and ventricular lead 14. The cardiac pacer 10 includes a header 16 and can 18, wherein a pulse generator 20 including pacing and sensing circuits 22 are contained therein. An indifferent electrode 24 of suitable known construction is positioned on the can 18 such that the indifferent electrode 24 is electrically isolated from the can 18 and is electrically coupled to the sensing circuit 22. Atrial lead 12 and ventricular lead 14 are engaged to header 16 and may be electrically coupled to the pulse generator 20 and pacing and sensing circuits 22 in a known suitable fashion. The atrial lead 12 is positioned in the atrium of the heart 26, wherein the atrial lead 12 includes a tip electrode 28 and ring electrode 30. The ventricular lead 14 is positioned within the ventricle of the heart 26, wherein the ventricular lead 14 includes a tip electrode 32 and ring electrode 34.

Figure 2:
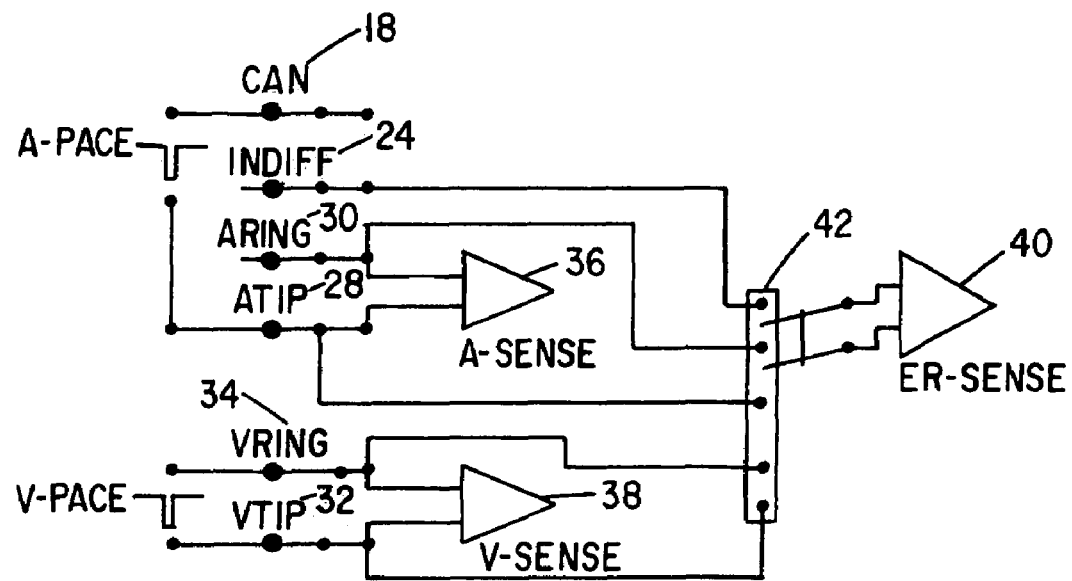
FIG. 2 is a schematic diagram of a portion of the cardiac pacing system's pacing/sensing circuitry in accordance with the present invention.

Referring now to FIG. 2 a portion of the pacing and sensing circuit 22 is shown. The circuit 22 includes an atrial intrinsic sense amplifier 36 electrically coupled between the atrial ring 30 and atrial tip 28. The circuit 22 also includes a ventricular intrinsic sense amplifier 38 electrically coupled between the ventricular ring electrode 34 and the ventricular tip electrode 32. A separate evoked response sense amplifier 40 is shown electrically coupled to a multi-switch 42, wherein the evoked response sense amplifier 40 may be electrically coupled to sense evoked response waveforms resulting from either an atrial pacing stimulus or ventricular pacing stimulus with any of the following sensing configurations: atrial ring to indifferent, atrial ring to ventricular tip, atrial ring to ventricular ring, atrial tip to ventricular ring, atrial tip to ventricular tip, atrial tip to indifference, ventricular ring to indifference, ventricular tip to indifference, and ventricular ring to ventricular tip. Those skilled in the art will appreciate that the preferred sensing configuration utilizing the separate evoked response sense amplifier 40 will vary depending upon whether the pacing stimulus is unipolar or bipolar and whether the pacing stimulus is directed in the atrium or ventricle. When unipolar pacing in the ventricle, the ventricular evoked response is preferably sensed between the ventricular ring to atrial tip electrodes, and alternatively, without limitation, may be sensed between the ventricular ring to indifferent, atrial tip to indifferent, or atrial ring to indifferent electrodes. When bipolar pacing in the ventricle, the ventricular evoked response is preferably sensed between the atrial tip and the conductive housing or can of the cardiac pacer, and alternatively, without limitation, may be sensed between the atrial tip to indifferent, atrial ring to can or atrial ring to indifferent electrodes. When unipolar pacing in the atrium, the atrial evoked response is preferably sensed between the atrial ring to indifferent and alternatively, without limitation, may be sensed between the atrial ring to ventricular tip, ventricular ring to indifferent, or ventricular tip to indifferent electrodes. When bipolar pacing in the atrium, the atrial evoked response is preferably sensed between the ventricular ring to can, and alternatively without limitation may be sensed between the ventricular ring to indifferent, ventricular tip to can, or ventricular tip to indifferent electrodes.

Figure 3:
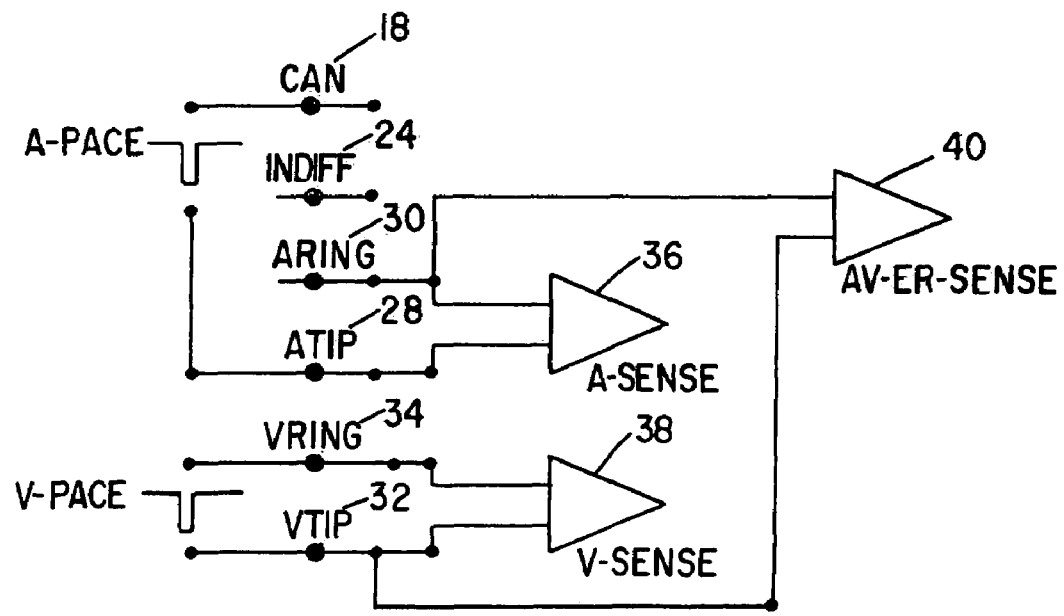
FIG. 3 is a schematic diagram of an alternate embodiment of a portion of the cardiac pacing system's pacing/sensing circuitry in accordance with the present invention.
Figure 4:
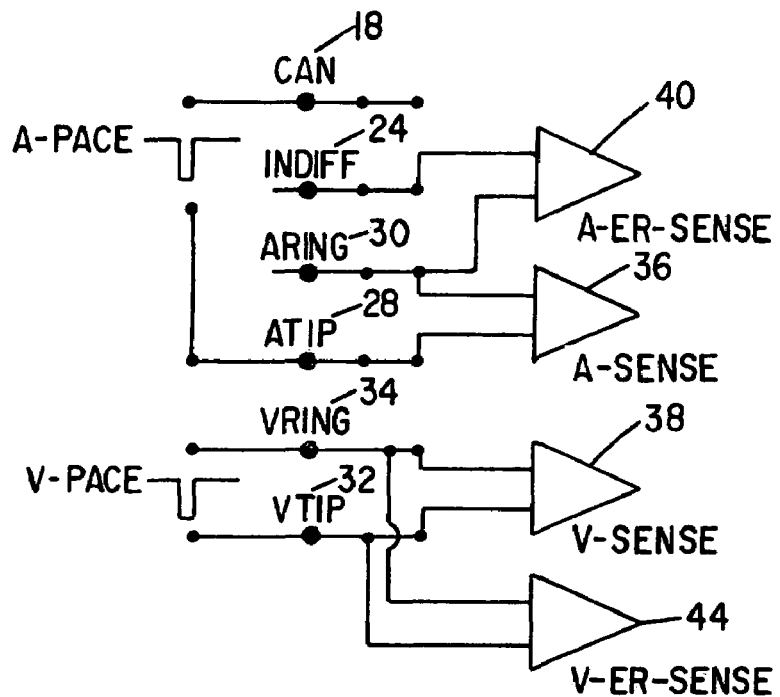
FIG. 4 is a schematic diagram of an alternate embodiment of a portion of the cardiac pacing system's pacing/sensing circuitry in accordance with the present invention.
Figure 5:
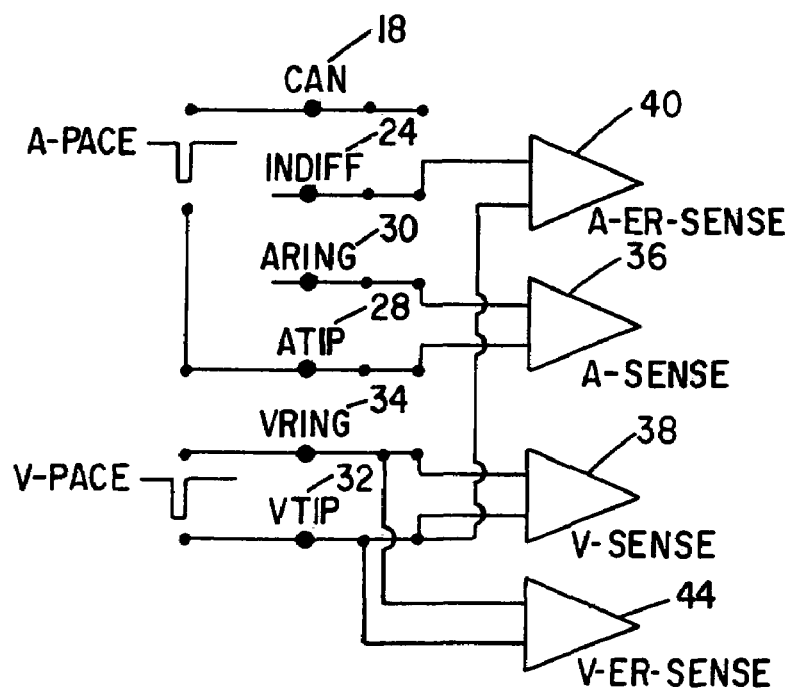
FIG. 5 is a schematic diagram of an alternate embodiment of a portion of the cardiac pacing system's pacing/sensing circuitry in accordance with the present invention.

Referring now to FIGS. 3–5 other alternate embodiments of a portion of the pacing/sensing circuit 22 are shown. FIG. 3 shows a dedicated atrial evoked response amplifier 40 electrically coupled between the atrial ring electrode 30 and the ventricular tip electrode 32. FIG. 4 shows an alternate embodiment of a portion of the pacing and sensing circuit 22, wherein the dedicated atrial evoked response amplifier 40 is electrically coupled between the atrial ring electrode 30 and the indifferent electrode 24 and a dedicated ventricular evoked response amplifier 44 is electrically coupled between the ventricular ring electrode 34 and the ventricular tip electrode 32. FIG. 5 shows an alternate embodiment of a portion of the pacing and sensing circuit 22, wherein the dedicated atrial evoked response amplifier 40 is electrically coupled between the indifferent electrode 24 and the ventricular tip electrode 32 and a dedicated ventricular evoked response amplifier 44 is electrically coupled between the ventricular ring electrode 34 and the ventricular tip electrode 32.

Figure 6:
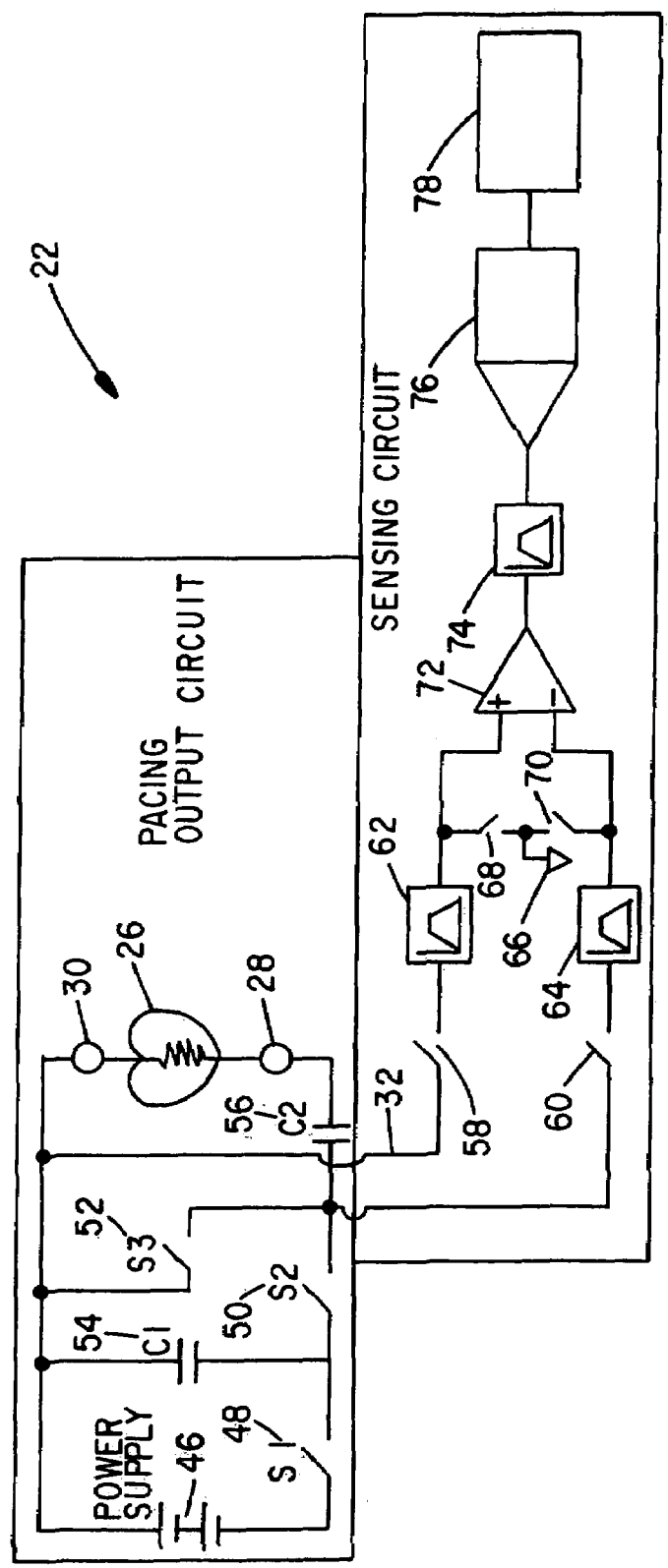
FIG. 6 is a schematic diagram of an alternate embodiment of a portion of the cardiac pacing system's pacing/sensing circuit of the present invention.

Referring now to FIG. 6, a portion of the embodiment of the pacing and sensing circuit 22 shown in FIG. 3 is illustrated in greater detail. Those skilled in the art will appreciate that pacing/sensing circuit may be modified slightly to achieve any of the above identified sensing configurations for atrial evoked response or any of the above identified sensing configurations for ventricular evoked response. Thus, the description of the pacing/sensing circuit as shown in FIG. 3 should not be construed as limiting. As will be explained below, the improved circuit 22 is capable of quickly attenuating any polarization voltages or "afterpotential" which result due to the application of stimulus pulses to the heart 26. By attenuating the polarization voltages or "afterpotential" in this fashion, the improved circuit 22 facilitates the task of capture verification in that the presence or absence of evoked responses may be readily determined without the masking caused by afterpotential. Capture verification advantageously allows the pacemaker 10 to automatically adjust the pacing output parameters so as to minimize power consumption while assuring therapeutic efficacy.

In the preferred embodiment, the circuit 22 of the present invention includes a power supply or battery, a first switch (S1) 48, a second switch (S2) 50, a third switch (S3) 52, a pacing charge storage capacitor (C1) 54, and an afterpotential reduction capacitor/coupling capacitor (C2) 56, all of which are cooperatively operable under the direction of a controller of known suitable construction. The power supply or battery 46 is preferably the battery provided to power the pacemaker 10 and may comprise any number of commercially available batteries suitable for pacing applications. The switches 48-52 are preferably carried out via any number of conventionally available microprocessor-directed semiconductor integrated circuit switching means. The pacing charge storage capacitor 54 may also comprise any number of conventional storage capacitors, but is preferably provided with a capacitance in the range of 10–30 microfarads so as to develop a sufficient pacing charge for stimulating the heart 26. The primary function of the coupling capacitor 56 is to quickly attenuate the polarization voltage or "afterpotential" which result from pacing and additionally block any DC signals from reaching the heart 26 during pacing. The coupling capacitor 56 has a capacitance in the range less than 5 microfarads, with a 2.2 microfarad capacitor being preferred.

The sensing portion of the circuit 22 includes pace blanking switches 58 and 60, passive filters 62 and 64, voltage reference 66, sense amplifier blanking switches 68 and 70, preamplifier 72, band pass filter 74, analog to digital converter 76 and detection comparator 78. The controller is operatively coupled to the circuit 22 and controls the opening and closing of switches 58, 60, 68, and 70. Although switches 58, 60, 68, and 70 are illustrated as discrete components, those skilled in the art will appreciate that they may comprise any number of commercially available microprocessor-directed semiconductor integrated circuit switching means. The pace blanking switches 58 and 60 are closed independently to detect an evoked response from the corresponding pacing electrode, and the shortening of the pacing afterpotential by using a reduced capacitance coupling capacitor allows pacing and sensing of the evoked response from the same electrodes. The intrinsic sensing channel may also be shared for efficient system operation. By shortening the pacing afterpotential, the recharge time of the coupling capacitor 56 may be reduced from a conventional time of greater than 20 milliseconds to under 10 milliseconds. This shortened time usually lapses before the onset of an evoked response. In turn, the sense amplifier blanking time may be reduced from a conventional 30 milliseconds to under 15 milliseconds with 12 milliseconds being preferred. This shortened blanking period in conjunction with the shortening of the pacing afterpotential increases the likelihood of detecting an evoked response.

Having described the constructional features of the pacing and sensing circuit the mode of use will next be described in greater detail. The controller implements a pre-programmed sequence to control the charging cycle, pacing cycle, and recharge cycle of the pacing output circuit. The charging cycle is characterized as having the first switch 48 in a closed state with the second switch 50 and third switch 52 in an open state. In this configuration, the pacing charge storage capacitor 54 may be charged up to a predetermined pacing voltage level, such as 3 volts. After the pacing charge storage capacitor 54 has been charged up to the predetermined pacing voltage level, the pacing cycle then operates to deliver the pacing charge from the pacing charge storage capacitor 54 to the heart 26.

To accomplish the pacing cycle, the first switch 48 is opened and third switch 52 remains opened and the second switch 50 is closed. This allows the voltage within the pacing charge storage capacitor 54 to be discharged through the coupling capacitor 56 to the tip electrode 28 positioned in the heart 26. The coupling capacitor 56 is less than 5 microfarads. This, once again, effectively blocks any significant DC signals from reaching the heart 26, while shortening the pacing afterpotential.

The recharge cycle involves keeping open the first switch 48 and opening the second switch 50 while closing the third switch 52. This allows the circuit 22 to passively recharge, such that the charge within the heart 26 is allowed to flow back into the pacing output circuit to balance out. During this passive recharge period, the charge on the coupling capacitor 56 is such that the signal decays over a short period of time and less than the required blanking period preceding detection of any evoked response from the heart 26. This is because the evoked responses from the heart 26 typically begins within 12 milliseconds from the delivery of a stimulus pulse to the atrium and within 20 milliseconds from the delivery of a stimulus pulse to the ventricle, which is substantially longer than the required recharge time. Advantageously, it has been found that reducing the overall capacitance of the coupling capacitor 56 quickly attenuates the polarization voltages or "afterpotentials" which result immediately following the application of a stimulus pulse such that the evoked responses within the heart 26 will not be masked or buried within the "afterpotential." By eliminating the adverse affects of "afterpotential" in this fashion, the pacemaker 10 can easily sense an evoked response and track the capture threshold of the heart 26 over time. Those skilled in the art will appreciate that with the continuous evaluation of an evoked response, the pacemaker 10 may be automatically adjusted to maintain an optimal pacing stimulus level which ensures safe pacing while minimizing power consumption.

Figure 7:
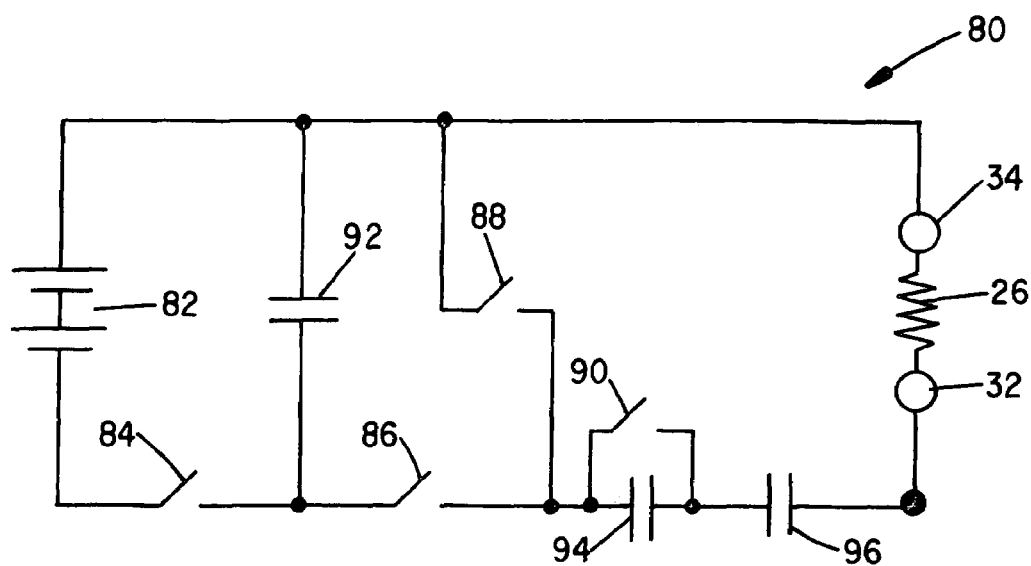
FIG. 7 is a schematic diagram of an alternate embodiment of the pacing output circuit of the present invention.

Refering now to FIG. 7, a portion of the pacing and sensing output circuit 22 is shown having a modified pacing circuit 80, wherein the circuit 80 is capable of quickly attenuating polarization voltages or "afterpotential" which result due to the application of stimulus pulses to the heart 26. By attenuating the polarization voltages or "afterpotential" in this fashion, the improved pacing circuit 80 of the present invention facilitates the task of capture verification in that the presence or absence of evoked responses may be readily determined without the masking caused by afterpotential. Capture verification may advantageously allow the pacemaker 10 to automatically adjust the capture threshold so as to minimize power consumption while assuring therapeutic efficacy.

The pacing output circuit 80 of the present invention includes a power supply or battery 82, a first switch 84, a second switch 86, a third switch 88, a fourth switch 90, a pacing charge storage capacitor 92, a first coupling capacitor 94, and a second coupling capacitor 96, all of which are cooperatively operable under the direction of a controller. By way of example, the improved pacing output circuit 80 is illustrated in a ventricular pacing arrangement for delivering stimulus pulses to the heart 26 via the tip electrode 32 and ring electrode 34 of the ventricular pacing lead 14 shown in FIG. 1. It is to be readily understood, however, that the improved pacing output circuit 80 of the present invention may also find application in an atrial pacing arrangement.

The power supply or battery 82 is preferably the battery provided to power the pacemaker 10 and may comprise any number of commercially available batteries suitable for pacing applications. The switches 84–90 are illustrated as discrete components but are preferably carried out via any number of commercially available microprocessor-directed semiconductor integrated circuit switching means. The pacing charge storage capacitor 92 may also comprise any number of commercially available storage capacitors, but is preferably provided with a capacitance in the range greater than 10 microfarads so as to develop a sufficient pacing charge for stimulating the heart 26.

One function of the second coupling capacitor 96 is to block DC signals from reaching the heart 26 during pacing. In order to minimize the pacing pulse droop the second coupling capacitor 96 should have a sufficiently large capacitance, for example, greater than 10 microfarads. In an important aspect of the present invention, the first coupling capacitor 94 is advantageously provided having a capacitance preferably less than 5 microfarads and substantially smaller than that of the second coupling capacitor 96. As will be described in greater detail below, the first coupling capacitor 94 may be selectively operable, via the fourth switch 90, so as to selectively reduce the effective capacitance of the second coupling capacitor 96, thereby quickly attenuating the polarization voltage or "afterpotential" which result from pacing.

Having described the constructional features of the modified pacing circuit 80, the operation of the pacing output circuit 80 will now be described. During a normal pacing mode, the pacing output circuit 80 engages in a charging cycle, a pacing cycle, and a recharge cycle. The charging cycle is characterized as having the first switch 84 in a closed state with the second and third switches 86–90 in an open state. In this configuration, the pacing charge storage capacitor 92 may be charged up to a predetermined pacing voltage level, such as 3 volts. After the pacing charge storage capacitor 92 has been charged up to the predetermined pacing voltage level, the pacing cycle then operates to deliver the pacing charge from the pacing charge storage capacitor 92 to the heart 26. To accomplish this pacing cycle, the first switch 84 and third switch 88 are in the open state and the second switch 86 and fourth switch 90 may be in the closed state. This allows the voltage within the pacing charge storage capacitor 92 to be discharged through the second coupling capacitor 96 to the tip electrode 32 of the pacemaker 10. Maintaining the fourth switch 90 in a closed state effectively bypasses the first coupling capacitor 94 such that the second coupling capacitor 96 is at its full capacitance level of approximately greater than 10 microfarads. This, once again, effectively blocks any DC signals from reaching the heart 26. In another alternate preferred embodiment, during the normal pacing mode, the fourth switch 90 may be open so long as the pacing threshold does not exceed a predetermined limit. In this manner detection of an evoked response (autocapture) may be enhanced during the normal pacing mode. During the autothreshold pacing mode, the fourth switch 90 is always in the open state and is closed for normal pacing.

The recharge cycle during normal pacing involves having the first switch 84 and the second switch 86 in the open state, while having the third switch 88 in the closed state. This allows the circuit 80 to passively recharge, such that the charge within the heart 26 is allowed to flow back into the circuit 80 to balance out. As noted above, during this passive recharge period, the charge on the second coupling capacitor 96 may be such that the afterpotential signal exponentially decays over a relatively long period of time lasting up to 100 milliseconds. This large "afterpotential" signal unwontedly masks out any evoked response from the heart 26. This is because the evoked responses from the heart 26 typically occur within 20 milliseconds from the delivery of the stimulus pulse to the ventricle and are substantially smaller in magnitude than the large "afterpotential" which would develop within the second coupling capacitor 96, were it not for the present invention.

It is an important aspect of the present invention that the polarization voltages or "afterpotential" which result from pacing quickly attenuate. This is achieved by having fourth switch 90 in the open state such that the first coupling capacitor 94 and second coupling capacitor 96 are connected in series. The series coupling of the first coupling capacitor 94 and second coupling capacitor 96 causes the overall capacitance to approximate the lower capacitance, or in other words, the capacitance of the first coupling capacitor 94. In a preferred embodiment, the first coupling capacitor 94 may be provided having a capacitance in the range of 1–2 microfarads such that, for a brief moment, the overall capacitance between the afterpotential reduction capacitor 94 and coupling capacitor 96 is approximately 1–2 microfarads. Advantageously, it has been found that reducing the effective capacitance of the second coupling capacitor 96 quickly attenuates the polarization voltages or "afterpotential" which result immediately following the application of a stimulus pulse such that the evoked responses within the heart 26 will not be masked or buried within the "afterpotential." By eliminating the adverse affects of "afterpotential" in this fashion, the pacemaker 10 can easily determine and track the capture threshold of the heart 26 over time.

Those skilled in the art will appreciate that with the continuous knowledge of the capture and pacing threshold in hand, the pacemaker 10 may be automatically adjusted to maintain an optimal pacing stimulus level which ensures safe pacing while minimizing power consumption.

Figures 8, 9:
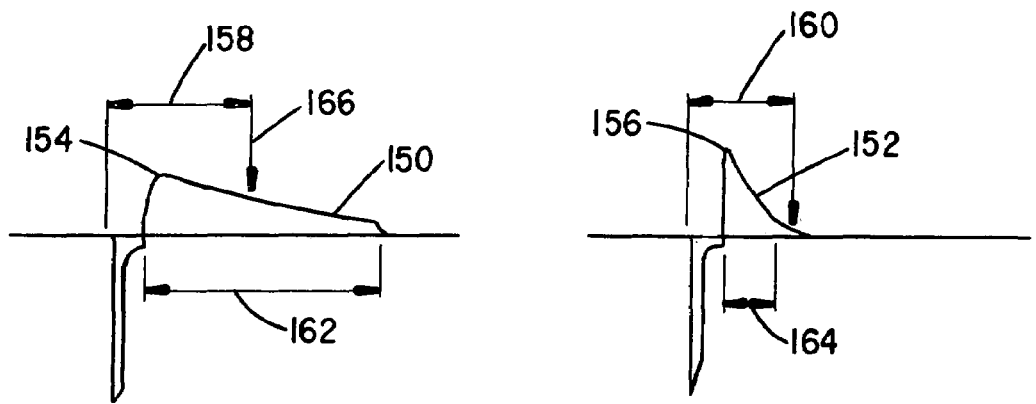
FIG. 8 depicts a resulting pacing waveform observable between the ring and tip of a pacing lead positioned within the heart of a patient, when utilizing a conventional pacing circuit.
FIG. 9 depicts a resulting pacing waveform observable between the ring and tip of a pacing lead positioned within the heart of a patient, when utilizing the afterpotential attenuation means of the present invention.

Referring next to FIGS. 8 and 9, the resulting pacing waveforms 150 and 152 detected with the tip and ring of a pacing lead, for the conventional pacing circuit and the pacing circuit of FIG. 8 respectively, are shown for comparison. By electrical analysis theory, familiar to those skilled in the art, the pacing afterpotential signal decay characteristics are determined by the time constant formed by the product of the coupling capacitor (blocking) and the load (a combination of the impedance of the lead body, electrode/tissue interface, and myocardium). When the capacitance of the coupling capacitor is reduced, the afterpotential has a larger initial amplitude but dissipates faster (compare afterpotential amplitudes 154 and 156 for the respective pacing afterpotential waveforms 150 and 152). The blanking period 158 before sensing for the conventional capacitor is greater than the required blanking period 160 when utilizing a 1 microfarad coupling capacitor (see FIGS. 8 and 9 for comparison). Also, the recharge time 162 when utilizing a conventional coupling capacitor is significantly longer than the required recharge time 164 required for the 1 microfarad capacitor. Further, the recharge time 162 overlaps into sensing period 166 for the conventional capacitor, whereas the recharge time 164 terminates prior to the beginning of the sensing period 168 for the 1 microfarad capacitor. Hence, when the coupling capacitance is sufficiently small, for example, less than 5 microfarads, the pacing afterpotential will settle to baseline at a faster rate and before the onset of the evoked response, thereby making detection of the evoked response feasible.

Those skilled in the art will appreciate that as the coupling capacitance decreases, the pacing pulse seen by the heart will bear a larger droop and the threshold voltage that evokes a response increases. Thus, if a small coupling capacitance is utilized during a determination of the threshold, the determined threshold will be greater than the actual threshold required during normal pacing (assuming that a conventional coupling capacitance is utilized during normal pacing), thereby increasing the pacing safety margin.

Figure 10:
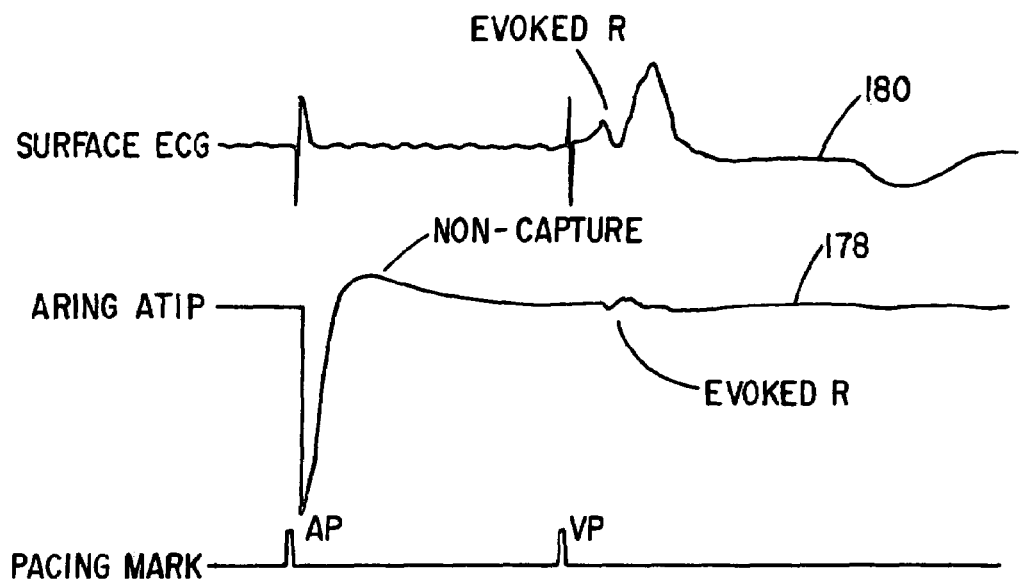
FIG. 10 depicts waveforms resulting from an atrial pacing stimulus and a ventricular pacing stimulus, wherein a first waveform is sensed with the atrial ring electrode and atrial tip electrode of the atrial pacing lead and a second waveform shown for comparison is sensed with a surface ECG, while utilizing a conventional coupling capacitor, and wherein the pacing output or stimulus is below the required threshold output.
Figure 11:
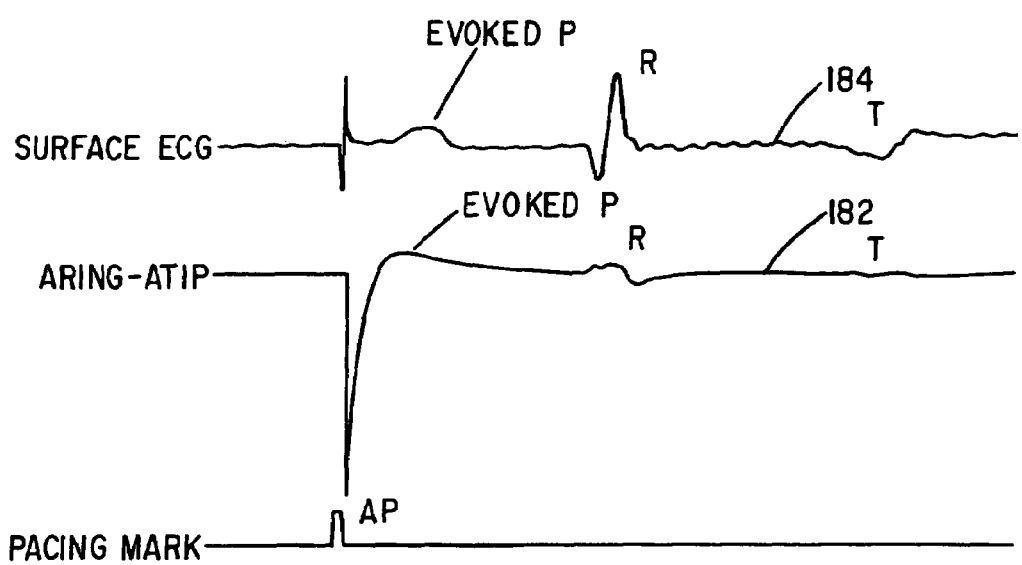
FIG. 11 depicts waveforms resulting from an atrial pacing output or stimulus, wherein the first waveform is sensed with the atrial ring electrode and atrial tip electrode of the atrial pacing lead and a second waveform shown for comparison is sensed with a surface ECG, while utilizing a conventional coupling capacitor, and wherein the pacing output is above the required threshold output.

Referring next to FIGS. 10 and 11, a recorded signal sensed between the atrial tip electrode 28 and the atrial ring electrode 30 resulting from a paced stimulus between the atrial tip electrode 28 and the atrial ring electrode 30 is shown, wherein a conventional coupling capacitor was utilized in the pacing and sensing circuit 22. FIG. 10 illustrates a resulting output or signal 178 and corresponding surface electrocardiogram (ECG) signal 180, wherein the pacing output voltage is below the known threshold. FIG. 11 illustrates a resulting signal 182 and corresponding ECG signal 184, wherein the pacing output voltage is above the known threshold. Those skilled in the art will appreciate that the intra cardiac signals 178 and 182 are overwhelmed with pacing afterpotential and, thus, the evoked response and non-captured artifacts during capture and non-capture respectively are not easily distinguishable within 100 milliseconds after pacing.

Figure 12:
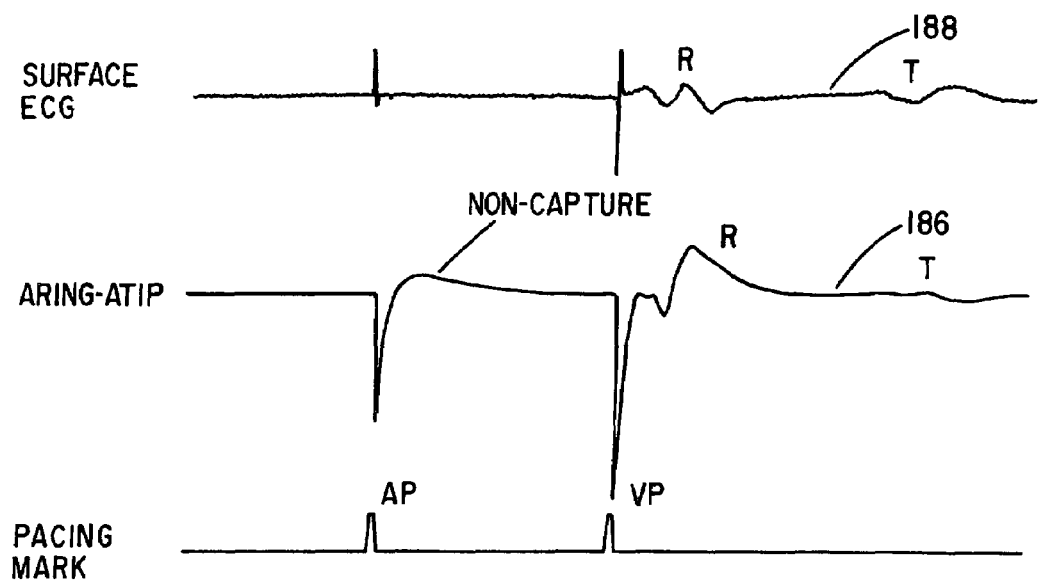
FIG. 12 depicts waveforms resulting from an atrial pacing output and a ventricular pacing output, wherein the first waveform is sensed with the atrial ring electrode and atrial tip electrode of the atrial pacing lead and a second waveform shown for comparison is sensed with a surface ECG, while utilizing the afterpotential attenuation means of the present invention, and wherein the pacing output is below the required threshold output.
Figure 13:
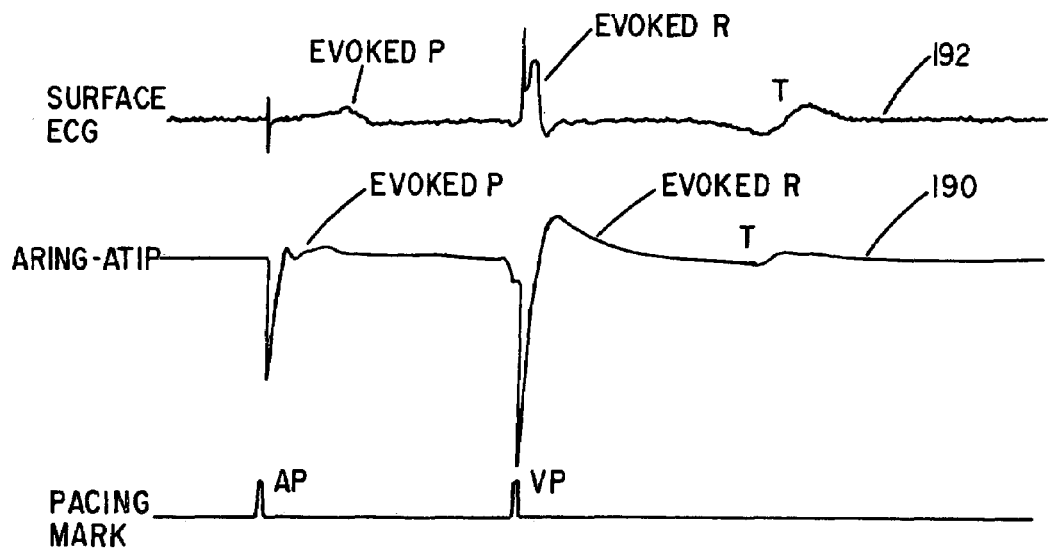
FIG. 13 depicts waveforms resulting from an atrial pacing output and a ventricular pacing output, wherein the first waveform is sensed with the atrial ring electrode and atrial tip electrode of the atrial pacing lead and a second waveform shown for comparison is sensed with a surface ECG, while utilizing the afterpotential attenuation means of the present invention, and wherein the pacing output is above the required threshold output.

FIGS. 12 and 13 show recorded signals sensed between the atrial tip electrode 28 and the atrial ring electrode 30 resulting from a paced stimulus between the atrial tip electrode 28 and the atrial ring electrode 30 received when implementing a 2 microfarad coupling capacitor having an 8 millisecond recharge time and a blanking time of 10 milliseconds. FIG. 12 illustrates a resulting output or signal 186 and corresponding surface electrocardiogram (ECG) signal 188, wherein the pacing output voltage is below the known threshold. FIG. 13 illustrates a resulting signal 190 and corresponding ECG signal 192, wherein the pacing output voltage is above the known threshold. The evoked response and non-captured artifacts are readily distinguishable during capture and non-capture for signals 186 and 190. Without limitation, a conventional peak detector may be adapted for detecting the peaks in the recorded signal received after pacing while using a 1 microfarad coupling capacitor having a 8 millisecond recharge time.

Figure 14:
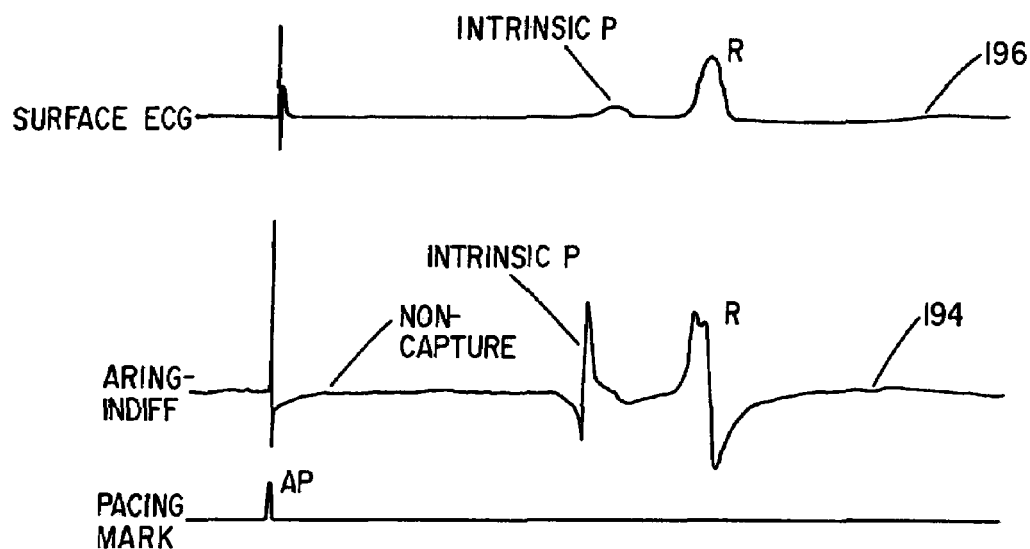
FIG. 14 depicts waveforms resulting from an atrial pacing output, wherein the first waveform is sensed with the atrial ring electrode and an indifferent electrode, and a second waveform shown for comparison is sensed with a surface ECG, while utilizing the afterpotential attenuation means of the present invention, and wherein the pacing output is below the required threshold output.
Figure 15:
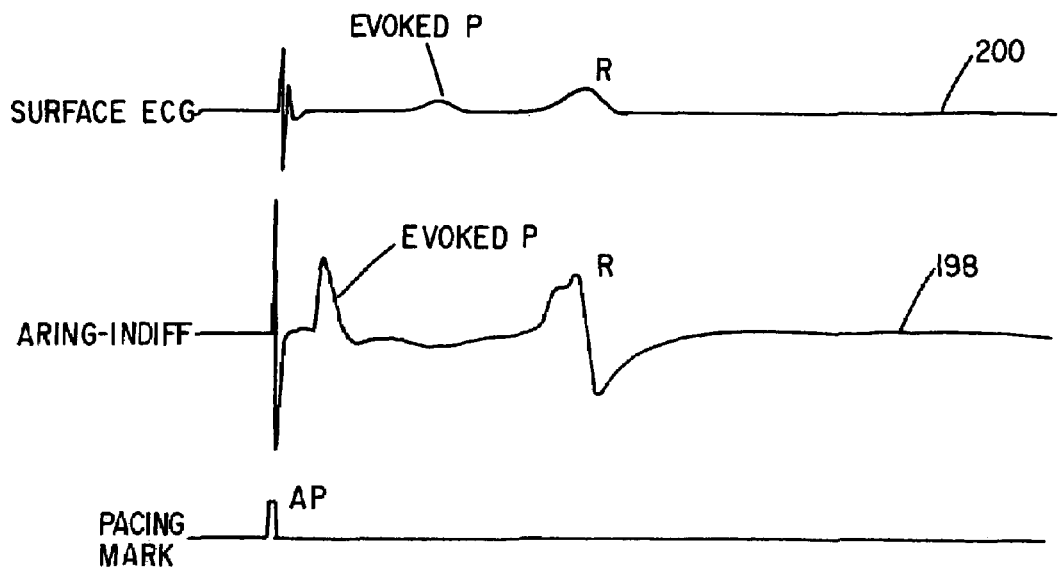
FIG. 15 depicts waveforms resulting from an atrial pacing output, wherein the first waveform is sensed with the atrial ring electrode and an indifferent electrode, and a second waveform shown for comparison is sensed with a surface ECG, while utilizing the afterpotential attenuation means of the present invention, and wherein the pacing output is above the required threshold output.
Figure 16:
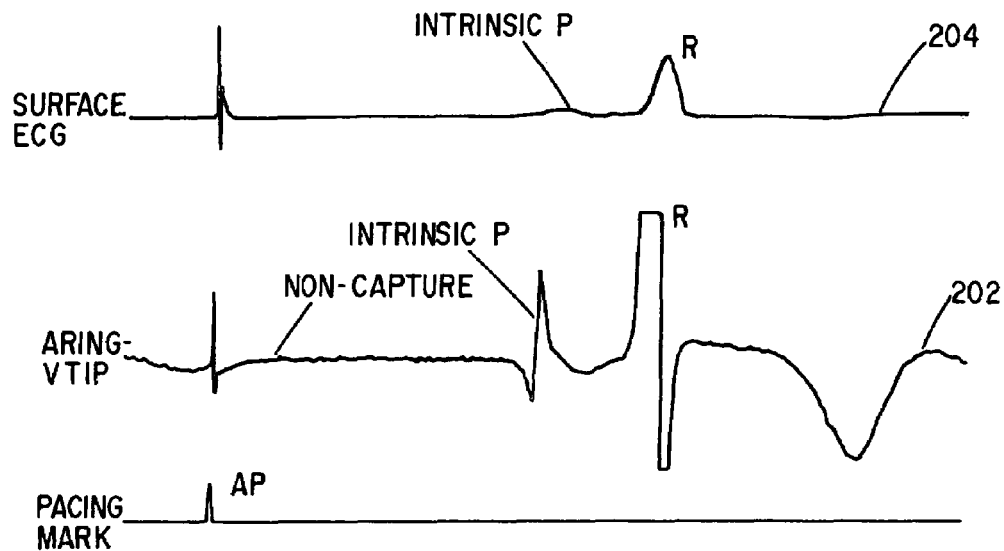
FIG. 16 depicts waveforms resulting from an atrial pacing output, wherein the first waveform is sensed with the atrial ring electrode and ventricular tip electrode, and a second waveforn shown for comparison is sensed with a surface ECG, while utilizing the afterpotential attenuation means of the present invention, and wherein the pacing output is below the required threshold output.

FIGS. 14 and 15 show recorded signals sensed between the atrial ring electrode 30 and the indifferent electrode 24 resulting from a paced stimulus between the atrial ring electrode 30 and the can 18. The recorded signals were received while implementing a 2 microfarad coupling capacitor having a 10 millisecond recharge time and a blanking time of 12 milliseconds. FIG. 14 illustrates a resulting output or signal 194 and corresponding surface electrocardiogram (ECG) signal 196, wherein the pacing output voltage is below the known threshold. FIG. 15 illustrates a resulting signal 198 and corresponding ECG signal 200, wherein the pacing output voltage is above the known threshold. The evoked response and non-captured artifacts are readily distinguishable during capture and non-capture for signals 194 and 198. As best seen in FIG. 16, the evoked response is readily distinguishable from output associated with polarization.

Figure 17:
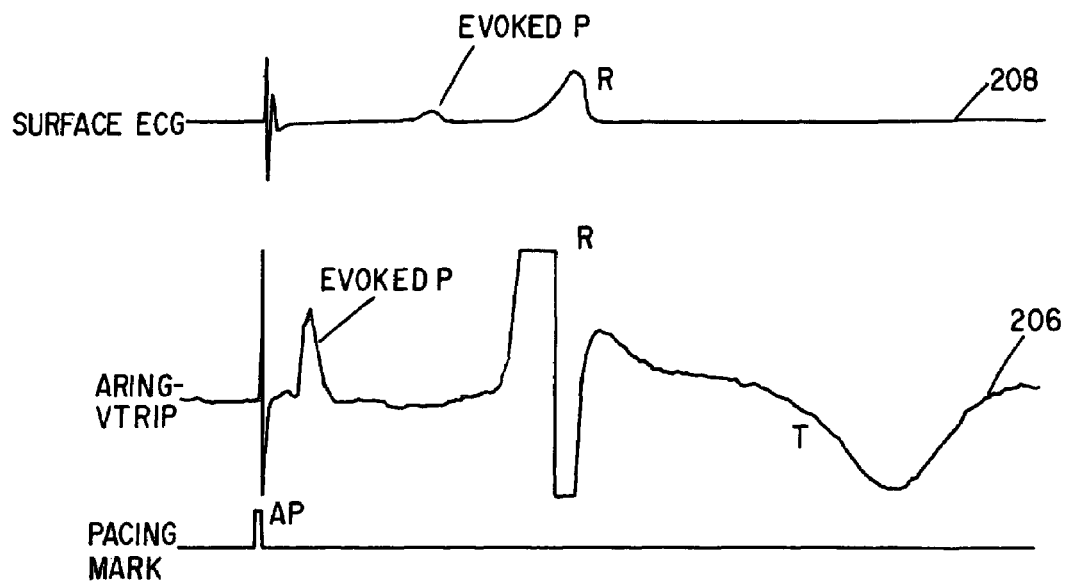
FIG. 17 depicts waveforms resulting from an atrial pacing output, wherein the first waveform is sensed with the atrial ring electrode and ventricular tip electrode, and a second waveform shown for comparison is sensed with a surface ECG, while utilizing the afterpotential attenuation means of the present invention, and wherein the pacing output is above the required threshold output.

FIGS. 16 and 17 show recorded signals sensed between the atrial ring electrode 30 and the ventricular tip electrode 32 resulting from a paced stimulus between the atrial ring electrode 30 and the can 18. The recorded signals were received while implementing a 2 microfarad coupling capacitor having a 10 millisecond recharge time and a blanking time of 12 milliseconds. FIG. 16 illustrates a resulting output or signal 202 and corresponding surface electrocardiogram (ECG) signal 204, wherein the pacing output voltage is below the known threshold. FIG. 17 illustrates a resulting signal 206 and corresponding ECG signal 208, wherein the pacing output voltage is above the known threshold. The evoked response and non-captured artifacts are readily distinguishable during capture and non-capture for signals 202 and 206. As discussed above, those skilled in the art will appreciate that noise is less likely to affect the recorded signal sensed between the atrial ring electrode 30 and ventricular tip electrode 32 and further the sensing configuration may also be utilized to detect a ventricular evoked response.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A cardiac pacing system for use with unipolar or bipolar atrial and ventricular pacing and sensing leads, said cardiac pacing system including:
    (a) at least an atrial lead having atrial electrodes comprising an atrial tip electrode and an atrial ring electrode electrically coupled thereto;
    (b) at least a ventricular lead having ventricular electrodes comprising a ventricle tip electrode and a ventricle ring electrode electrically coupled thereto;
    (c) pacing means for providing a pacing stimulus to at least one of an atrium or ventricle of a heart, said pacing means electrically coupled to at least one of said atrial lead and said ventricular lead;
    (d) sensing means for sensing a response evoked by the pacing stimulus, said sensing means electrically coupled to at least one of said atrial lead and said ventricular lead said sensing means including multiple independent blanking switches corresponding to independent electrodes;
    (e) an indifferent electrode and an electrically conductive can that contains the pacing and sensing means, said indifferent electrode being positioned on the can;
    (f) afterpotential attenuation means for attenuating afterpotentials which result due to the application of the pacing stimulus to the heart by said cardiac pacing system, said afterpotential attenuation means being electrically coupled to said pacing means and including first coupling capacitor means for attenuating afterpotential operatively coupled to second coupling capacitor means for blocking DC components, and also including switching means for selectively coupling said second coupling capacitor means in series with said first coupling capacitor means so as to reduce the effective capacitance of said second coupling capacitor means, said system having a combined reduced coupling capacitance of less than 5 microfarads; and
    (g) wherein the sensing means is adapted to selectively sense evoked responses between all combinations of any two of said electrodes.

2. A cardiac pacing system as in claim 1 wherein the signal associated with the evoked response is sensed between the atrial tip electrode and the indifferent electrode.

3. A cardiac pacing system as in claim 1, wherein the signal associated with the evoked response is sensed between the ventricular ring electrode and the ventricular tip electrode.

4. A cardiac pacing system as in claim 1, wherein the signal associated with the evoked response is sensed between the atrial ring electrode and the indifferent electrode.

5. A cardiac pacing system as in claim 1, wherein the signal associated with the evoked response is sensed between the ventricular tip electrode and the indifferent electrode.

6. A cardiac pacing system as recited in claim 1, wherein the signal associated with the evoked response is sensed between the ventricular ring electrode and the indifferent electrode positioned on a can of the cardiac pacer and electrically coupled to the cardiac pacer.

7. A cardiac pacing system as in claim 1, wherein the signal associated with the evoked response is sensed between the atrial ring electrode and one of the ventricular electrodes.

8. A cardiac pacing system as in claim 1, wherein the signal associated with the evoked response is sensed between the atrial tip electrode and one of the ventricular electrodes.

9. A cardiac pacing system as in claim 1, wherein the signal associated with the evoked response is sensed between the ventricular ring electrode and the atrial tip electrode.

10. A cardiac pacing system as in claim 1, wherein the signal associated with the evoked response is sensed between the atrial tip electrode arid the electrically conductive housing of the cardiac pacing system.

11. A cardiac pacing system as in claim 1, wherein the signal associated with the evoked response is sensed between the atrial ring electrode and the electrically conductive housing of the cardiac pacing system.

12. A cardiac pacing system as in claim 1, wherein the signal associated with the evoked response is sensed between the atrial ring electrode and the ventricular tip electrode.

13. A cardiac pacing system as in claim 1, wherein the signal associated with the evoked response is sensed between the ventricular ring electrode and the electrically conductive housing of the cardiac pacing system.

14. A cardiac pacing system as in claim 1, wherein the signal associated with the evoked response is sensed between the ventricular tip electrode and the electrically conductive housing of the cardiac pacing system.

15. A cardiac pacing system as in claim 1, wherein said first coupling capacitor means has a substantially smaller capacitance than said second coupling capacitor means.

16. A cardiac pacing system as in claim 1, wherein said second coupling capacitor means has a capacitance ranging from 10–40 microfarads, and said first coupling capacitor means has a capacitance less than 5 microfarads.

17. A cardiac pacing system for use with unipolar or bipolar atrial and ventricular pacing and sensing leads, said cardiac pacing system including:
(a) at least an atrial lead having atrial electrodes comprising an atrial tip electrode and an atrial ring electrode electrically coupled thereto;
(b) at least a ventricular lead having ventricular electrodes comprising a ventricle tip electrode and a ventricle ring electrode electrically coupled thereto;
(c) a pacing circuit including a pacing charge storage capacitor that provides a pacing stimulus to at least one off an atrium or ventricle of a heart, said pacing circuit electrically coupled to at least one of said atrial lead and said ventricular lead;
(d) a sensing circuit that senses a response evoked by the pacing stimulus, said sensing circuit electrically coupled to at least one of said atrial lead and said ventricular lead, said sensing circuit including multiple independent blanking switches corresponding to independent electrodes;
(e) an indifferent electrode and an electrically conductive can that contains the pacing and sensing means, said indifferent electrode being positioned on the can;
(f) a plurality of coupling capacitors electrically coupled together including a first coupling capacitor that attenuates afterpotential, operatively coupled to a second coupling capacitor that blocks DC components, and also includes switches for selectively coupling said second coupling capacitor in series with said first coupling capacitor so as to reduce the effective capacitance of said second coupling capacitor, wherein a capacitance of the capacitors coupled together has a combined reduced capacitance of less than 5 microfarads wherein the combined reduced capacitance of less than 5 microfarads attenuates afterpotentials which result due to the application of the pacing stimulus to the heart by said cardiac pacing system, said capacitors being electrically coupled to said pacing circuit; and
(g) wherein the sensing circuit is adapted to selectively sense evoked responses between all combinations of any two of said electrodes.

18. A cardiac pacing system as in claim 17 wherein the signal associated with the evoked response is sensed between the atrial tip electrode and the indifferent electrode.

19. A cardiac pacing system as in claim 17, wherein the signal associated with the evoked response is sensed between the ventricular ring electrode and the ventricular tip electrode.

20. A cardiac pacing system as in claim 17, wherein the signal associated with the evoked response is sensed between the atrial ring electrode and the indifferent electrode.

21. A cardiac pacing system as in claim 17, wherein the signal associated with the evoked response is sensed between the ventricular tip electrode and the indifferent electrode.

22. A cardiac pacing system as in claim 17, wherein the signal associated with the evoked response is sensed between the ventricular ring electrode and the indifferent electrode.

23. A cardiac pacing system as in claim 17, wherein the signal associated with the evoked response is sensed between the atrial ring electrode and one of the ventricular electrodes.

24. A cardiac pacing system as in claim 17, wherein the signal associated with the evoked response is sensed between the atrial tip electrode and one of the ventricular, electrodes.

25. A cardiac pacing system as in claim 17, wherein the signal associated with the evoked response is sensed between the ventricular ring electrode and the atrial tip electrode.

26. A cardiac pacing system as in claim 17, wherein the signal associated with the evoked response is sensed between the atrial tip electrode and the electrically conductive housing of the cardiac pacing system.

27. A cardiac pacing system as in claim 17, wherein the signal associated with the evoked response is sensed between the atrial ring electrode and the electrically conductive housing of the cardiac pacing system.

28. A cardiac pacing system as in claim 17, wherein the signal associated with the evoked response is sensed between the atrial ring electrode and ventricular tip electrode.

29. A cardiac pacing system as in claim 17, wherein the signal associated with the evoked response is sensed between the ventricular ring electrode and the electrically conductive housing of the cardiac pacing system.

30. A cardiac pacing system as in claim 17, wherein the signal associated with the evoked response is sensed between the ventricular tip electrode and the electrically conductive housing of the cardiac pacing system.

31. A cardiac pacing system as in claim 17, wherein said first coupling capacitor has a substantially smaller capacitance than said second coupling capacitor.

32. A cardiac pacing system as in claim 17, wherein said second coupling capacitor has a capacitance ranging from 10–40 microfarads, and said first coupling capacitor has a capacitance less than 5 microfarads.

* * * * *